United States Patent [19]

Zerbe

[11] Patent Number: 4,800,084

[45] Date of Patent: Jan. 24, 1989

[54] PHARMACEUTICAL PRODUCT IN THE FORM OF A PELLET WITH CONTINUOUS, DELAYED MEDICAMENT SUBSTANCE EMISSION

[76] Inventor: Horst Zerbe, Wilhelm-Busch-Str. 4, D-4282 Velen, Fed. Rep. of Germany

[21] Appl. No.: 86,178

[22] Filed: Aug. 13, 1987

Related U.S. Application Data

[63] Continuation of Ser. No. 694,245, Jan. 24, 1985, abandoned.

[30] Foreign Application Priority Data

Feb. 1, 1984 [DE] Fed. Rep. of Germany ....... 3403329

[51] Int. Cl.$^4$ .......................... A61K 9/20; A61K 9/28
[52] U.S. Cl. ..................................... 424/458; 424/461; 424/467; 424/471; 424/474; 424/495; 424/497
[58] Field of Search ............... 424/458, 461, 462, 471, 424/474, 495, 497

[56] References Cited

U.S. PATENT DOCUMENTS

| | | |
|---|---|---|
| 2,853,420 | 9/1958 | Lowey .................................. 424/35 |
| 2,928,770 | 3/1960 | Bardani ................................ 424/35 |
| 2,963,402 | 9/1960 | Nalin et al. ......................... 424/35 |
| 2,996,431 | 8/1961 | Barry ................................... 424/35 |
| 3,247,066 | 4/1966 | Milosovich ......................... 424/35 |
| 3,344,029 | 9/1967 | Berger ................................ 424/19 |
| 3,538,214 | 11/1970 | Poll et al. ........................... 424/35 |
| 3,835,221 | 9/1974 | Fulberth et al. .................... 424/20 |
| 3,935,326 | 1/1976 | Groppenbacher et al. ......... 424/35 |
| 4,083,949 | 4/1978 | Benedikt ............................. 424/19 |
| 4,309,405 | 1/1982 | Guley et al. ........................ 424/21 |
| 4,309,406 | 1/1982 | Guley et al. ........................ 424/21 |
| 4,330,338 | 5/1982 | Banker ................................ 424/35 |
| 4,341,759 | 7/1982 | Bogentoft et al. ................. 424/21 |
| 4,415,547 | 11/1983 | Yu et al. ............................. 424/19 |

Primary Examiner—Shep K. Rose
Attorney, Agent, or Firm—Dennis P. Clarke

[57] ABSTRACT

The discovery presented herewith concerns a pharmaceutical product in the form of a pellet with improved continous, delayed medicament substance emission through a coating, which is made of a material that does not dilute in gastric and intestinal juices and which is impermeable for gastric and intestinal juices and which tightly seals the core made of material that is dilutable in gastric and intestinal juices.

10 Claims, 2 Drawing Sheets

PHARMACEUTICAL PRODUCT IN THE FORM OF A PELLET WITH CONTINUOUS, DELAYED MEDICAMENT SUBSTANCE EMISSION

This is a continuation of application Ser. No. 694,245 filed Jan. 24, 1985 now abandoned.

The present discovery concerns a pharmaceutical product in the form of a pellet with continuous, but delayed medicament substance emission.

BACKGROUND OF THE INVENTION

To a very significant degree, pharmaceutical substances are administered in the form of so-called pellets. In order to achieve a delayed emission of the effective substance, the pellet containing the substance is coated with a layer made of such a material that the gastric and intestinal juices release the substance from the pellet at a slow rate in accordance with diffusion principles. To a relevant degree, the pellet usually consists of pre-fabricated cores made of a material that dilutes in gastric and intestinal juices, for example with starch or similar sugar crystal compounds (saccharose crystals), upon which is the depository coating, which contains the medicament substance, and finally the outer coating, which causes the continuous, delayed medicament substance emission, are applied. Finally, very often another outer coating, also containing the medicament substance, is applied from which the medicament substance is absorbed immediately after the pellet has been administered and, thereby, an initial dosage of the substance is released to achieve a certain, desired medicament substance level in the circulatory system.

The task of this form of preparation is to provide continuous and delayed of medicament substance emission, while maintaining the desired blood absorption level over the entire determined period of time, and an essentially complete emission of substance from the product, if applicable, after achieving a desired initial substance level in the circulatory system of the patient for a predetermined period of time, e.g., for a number of hours.

The solution of this task for such types of pellets, however, is disturbed by the fact that the outer coating, which causes the continuous and delayed substance emission, perforates prematurely after the pellet has been administered so that the medicament substance still contained in the pellet is prematurely released through the preforations, contrary to the desired continuity and delay in substance emission so that for a portion of the predetermined period of time, the medicament substance level in the blood system is below the desired level.

Many attempts have been undertaken in the pharmaceutical industry to solve this problem. The material composing the outer coating has been changed, but elimination of the problems of such types of pellets has not been achieved.

BRIEF SUMMARY OF THE INVENTION

The pharmaceutical product, containing a medicament substance, proposed by the present discovery comprises a pellet with as continuous, delayed, and essentially complete emission of the substance contained therein over a predetermined period of time consists, of a core made of a material that dilutes in gastric and intestinal juices, of a depository coating surrounding the core and containing the medicament substance, and of a coating, which causes and controls the continuous, delayed medicament emission over a determined period of time, and, if applicable, of another outer coating, which contains the active substance and is not protected against gastric and intestinal juices, for achieving a desired initial substance level in the circulatory system. The administration of such pellets is known for instance from Joseph R. Robinson, Sustained and Controlled Release Drug Delivery Systems (1978), Marcel Dekker, Inc., New York, for instance at chapter 3, Methods to Achieve Sustained Drug Delivery, the physical approach: oral and parenteral dosage forms, pp. 123 to 209 and U.S. Pat. No. 2,963,402. The disclosures of these references are incorporated herein by reference. The invention is characterized by the fact that a coating, that is made of a material that does not dilute in gastric and intestinal juices, which is impermeable for gastric and intestinal juices and which tightly seals the core, is applied between the depository coating, which contains the substance, and the core made of a material that dilutes in gastric and intestinal juices.

BRIEF DESCRIPTION OF THE DRAWINGS

The invention will be described in reference to the drawings wherein.

DETAILED DESCRIPTION OF THE INVENTION

Experts are aware of materials that do not dilute in gastric and intestinal juices. Of particular preference, the intermediary coating consists of a material that does not dilute in gastric and intestinal juices made of ethyl cellulose with an ethoxyl content of 47.5% to 49%. Other especially suitable materials are polyvinyl acetate, anionic polymer compounds made of methacrylic acid and methacrylic acid esters, acrylic and methacrylic acid ester copolymer compounds, shellac as well as mixtures of these substances. The core of the pellet proposed by the discovery consists, as previously set forth, as saccharose or saccharose combined with starch syrup.

The coating, which surrounds the depository coating containing the medicament substance and which controls and causes continuous and delayed substance emission for a prescribed period of time, preferably consists of the same basic substances as the aforedescribed intermediary coating made of a material that does not dilute in gastric and intestinal juices. It also contains pore-forming substances which are also familiar to experts in the field. Of particular preference for this are polyethylene glycols. Other suitable materials are polyvinyl pyrrolidon, hydroxy propyl methyl cellulose, hydroxypropyl cellulose as well as mixtures of these substances. The type and amount of these additives depend, in a known way, upon the speed with which the substance is supported to be released from he depository coating.

Without limiting the discovery, substances for which the product proposed by the discovery can especially be used are isocorbide-5-nitrate, isosorbide dinitrate and captopril.

In order to guarantee the bonding of the depository coating and of the initial coating and to prevent the destruction of these coatings by mechanical stresses, adhesive polymers, which dissolve in water, can be used during the production of these coatings. The physiologically compatible substances that could be used for such a process are known to the experts in the field.

Surprisingly, following an immediate initial dose or a dose for achieving a desired initial substance level in the blood circulatory system in the patient, to the extent that an unprotected outer coating containing the substances is used in this instance, the pellets proposed by the discovery showed a practically complete continuous, delayed substance emission and also an essentially complete emission of the substance contained in the pellet. By using the pellet proposed by the discovery, initially the desired initial substance blood level is achieved and the pellet then essentially releases continuously as much substance as required for maintaining desired substance level in the circulatory system over the desired time period.

Figure 1:
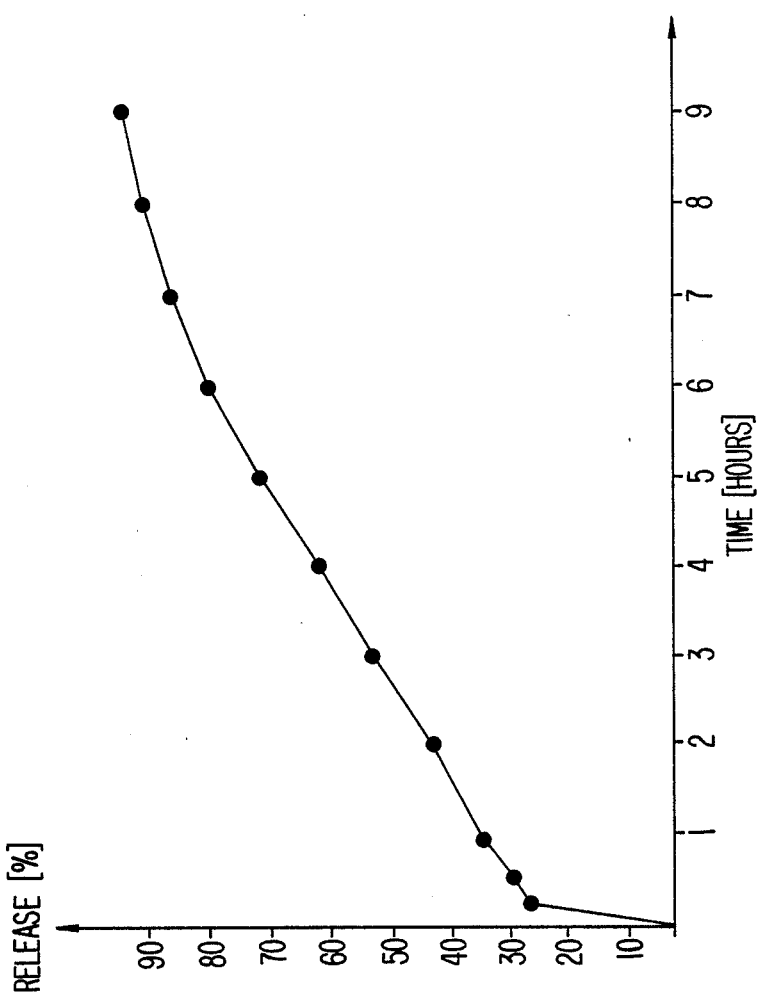
FIG. 1 is a chart showing substance release in percent relative to time in hours.

This is based on the pellet, proposed by the discovery and depicted in FIG. 1, for isosorbide-5-nitrate (5-ISN). As can be seen from the diagram, a practically complete continuous substance flow is possible in the patient without the patient having to take other forms of medication a number of times over the prescribed period of time.

Figure 2:
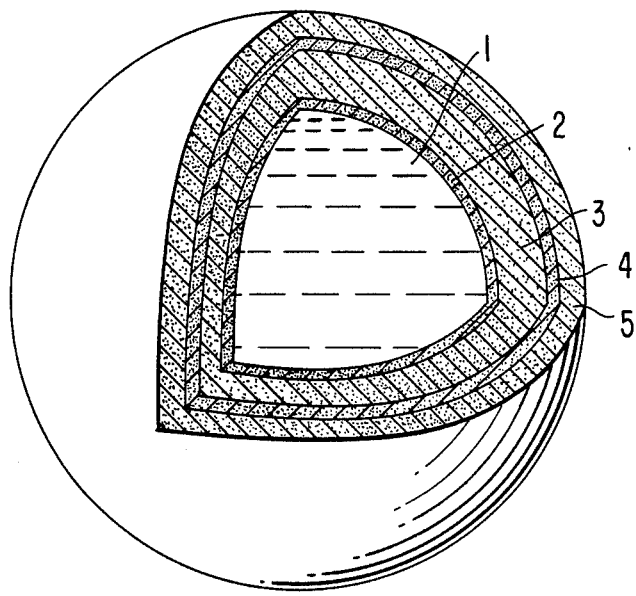
FIG. 2 is an illustration of a pellet constructed in accordance with the invention.

FIG. 2 depicts the structure of the pellet described by the discovery. The core 1 made of sugar crystals is tightly sealed by the insulating coating 2 made of ethyl cellulose with an ethoxyl content of 47.5 to 49% so that no gastric and intestinal juices can penetrate into the sugar core 1. The substance is contained in the depository coating 3, which in turn is surrounded by the outer coating 4, which also contains about 10% of polyethylene glycol in addition to the coating material of the insulating coating 2 as a pore-former. The depository coating 3 contains 70% of all isosorbide-5-nitrate contained in the pellet. The outer coating 5, which is unprotected against the effects of gastric and intestinal juices, contains 30% of the substance so that once the pellet is swallowed the desired level of medication is reached in the circulatory system of the patient.

EXAMPLE 1

A pharmaceutical product, in accordance with the present discovery is produced in the following fashion:

A suspension, consisting of 100 g ethyl cellulose, 20 g talcum powder, 475 ml ethyl alcohol, 475 ml methylene chloride, is sprayed, with the aid of a spraying mechanism, onto sugar balls of 1000 g in weight with a particle diameter of 0.6–0.71 mm.

Then, 1500 g of a mixture made of 9 parts of isosorbide-5-nitrate and one part of lactose and 570 ml of water are added to the insulated sugar balls while using an adhesive solution made of 57 g of hydroxypropyl cellulose.

By means of a suitable spraying mechanism, a suspension, consisting of 196.6 g ethyl cellulose; 19.66 g polyethylene glycol; 49.2 g talcum; 950 ml ethyl alcohol; 950 ml methylene chloride is sprayed onto 2000 g of these pellets. 420 g of a mixture made of 9 parts isosorbide-5-nitrate and one part of lactose and 200 ml of water is applied to 2000 g of these pellets with the aid of a solution consisting of 20 g hydroxypropyl cellulose.

Substance Release

The substance release profile was established on the basis of the pellets produced in accordance with the method depicted in Example 1, which corresponds to a medicament substance content of about 100 mg. In order to take physiological conditions into account, artificial gastric juice and then artificial intestinal juices were used as a test medium during the first two hours. The volume of test media was selected in such a way that sink conditions were maintained over the course of the test. The release amounts of isosorbide-5-nitrate was determined fluid chromatographically at fixed time intervals. The results are graphically depicted in FIG. 1.

I claim:

1. In a pharmaceutical product in the form of a pellet, said product allowing a continuous, delayed, essentially complete emission of a pharmaceutically active agent over a predetermined period of time upon administration to a patient in need thereof, the improvement wherein said pharmaceutical product consists essentially of:
   (a) a core consisting essentially of a pharmaceutically inert material that dissolves in gastric and intestinal juices,
   (b) a layer comprising said pharmaceutically active agent and surrounding said core, and
   (c) an outer pharmaceutically inert coating on said pharmaceutically active agent containing layer, said outer coating conrolling and causing the continuous delayed emission of said pharmaceutically active agent upon administration and,
   (d) an outer coating containing a pharmaceutically active agent unprotected against the influence of gastric and intestinal juices, and between said core of pharmaceutically inert material dissolving in the gastric and intestinal juices and said layer containing the active agent and surrounding said core, providing a pharmaceutically inert layer which is impermeable to gastric and intestinal juices and which forms a tight seal around said core.

2. Pharmaceutical product in accordance with claim 1 wherein said layer around the core and forming a tight seal there around impermeable to gastric and intestinal juices, consists of a member selected from the group consisting of ethyl cellulose with an ethoxyl content of 47.5 to 49 per cent, polyvinyl acetate, an anionic polymer compound made of methacrylic acid and methacrylic acid esters, an acrylic and methacrylic acid ester copolymer compound, shellac and mixtures of several such compounds.

3. Pharmaceutical product according to claim 1 wherein said layer forming a tight seal around said core and impermeable to gastric and intestinal juices, consists of ethyl cellulose with an ethoxyl content of 47.5 to 49 per cent.

4. Pharmaceutical product according to claim 1 wherein said outer coating on said active agent comprises a layer made of the same material as said layer forming a tight seal around the core, said outer coating forming material having a pore-forming substance mixed thereinto.

5. Pharmaceutical product according to claim 4 wherein the pore-forming substance is polyethylene glycol.

6. Pharmaceutical product according to claim 2 wherein said outer coating on said active agent comprises a layer made of the same material as said layer forming a tight seal around the core, said outer coating forming material having a pore-forming substance mixed thereinto.

7. Pharmaceutical product according to claim 6 wherein the pore-forming substance is polyethylene glycol.

8. Pharmaceutical product according to claim 3 wherein said outer coating on said active agent comprising layer is made of the same material as said layer forming a tight seal around the core, said outer coating forming material a pore-forming substance mixed thereinto.

9. Pharmaceutical product according to claim 8 wherein the pore-forming substance is polyethylene glycol.

10. Pharmaceutical product according to any of claims 4, 6 or 8 wherein said outer coating forming material has about ten percent of said pore-forming.

* * * * *